United States Patent [19]

Taupin

[11] 4,106,119

[45] Aug. 15, 1978

[54] EYE-SHADES

[76] Inventor: Jean-Paul Taupin, Le Vivier, 58140 Urzy, France

[21] Appl. No.: 521,204

[22] Filed: Nov. 5, 1974

[30] Foreign Application Priority Data

Nov. 8, 1973 [FR] France ................................ 73 39794

[51] Int. Cl.² .............................................. A61F 9/04
[52] U.S. Cl. ........................................................ 2/12
[58] Field of Search ....................... 2/12, 13, 14 F, 15, 2/433; 273/190 A

[56] References Cited

U.S. PATENT DOCUMENTS

| | | | |
|---|---|---|---|
| 1,809,956 | 6/1931 | Wrenshall | 2/12 |
| 2,385,405 | 9/1945 | Crowther | 2/12 |
| 2,433,590 | 12/1947 | Barr | 2/12 |
| 2,988,743 | 6/1961 | Wagenfeld | 2/12 |
| 3,308,478 | 3/1967 | Tate | 2/12 |

FOREIGN PATENT DOCUMENTS

| | | | |
|---|---|---|---|
| 1,025,669 | 1/1953 | France | 2/12 |
| 296,403 | 5/1932 | Italy | 2/12 |
| 290,771 | 5/1928 | United Kingdom | 2/12 |

*Primary Examiner*—Peter Nerbun
*Attorney, Agent, or Firm*—Lewis H. Eslinger

[57] ABSTRACT

This invention relates to eye-shades, particularly those for use in practicing certain sports where it is necessary to concentrate the wearer's vision upon an object e.g. a target.

According to the invention, an eye-shade comprises a substantially flat brow member, a temple member depending from each lateral portion of said brow member and a head-encompassing member interconnecting said temple members. The brow member extends outwardly in a substantially horizontal attitude above the wearer's eyes in the position of use with the temple members assuming a substantially vertical attitude: the brow member and the temple members between them define a field of vision within the three faces constituted by the said members: means are provided to hold said temple members in position against the wearer's temples.

Conveniently, the head encompassing member is in the form of a head band which in itself constitutes said means for holding said temple members against the wearer's temples.

2 Claims, 8 Drawing Figures

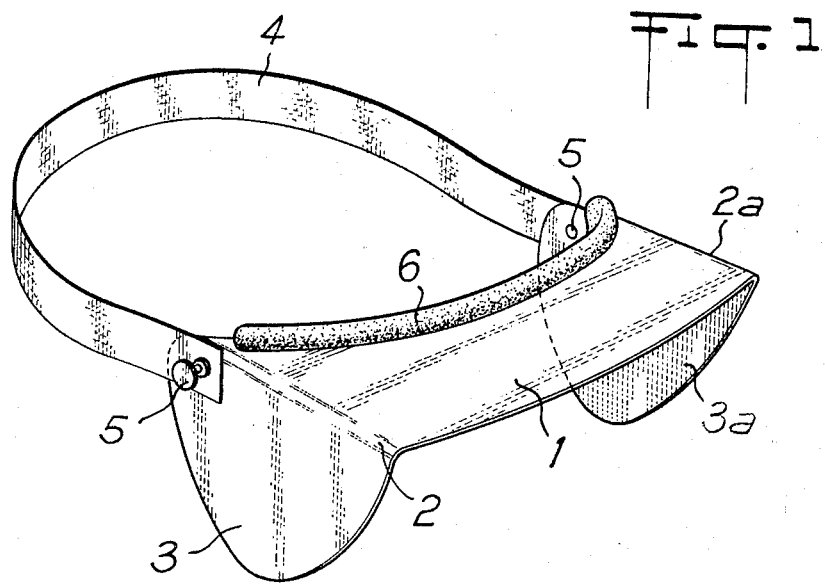
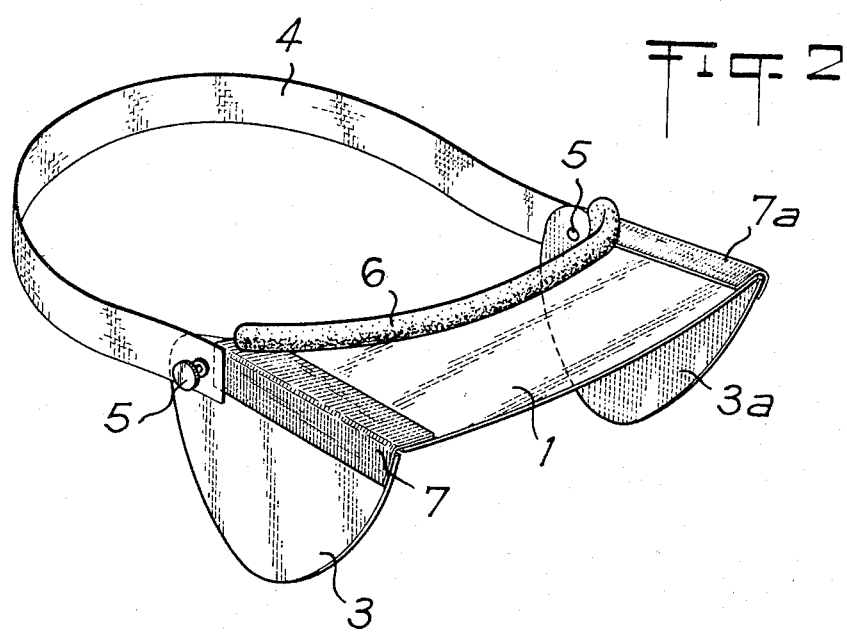

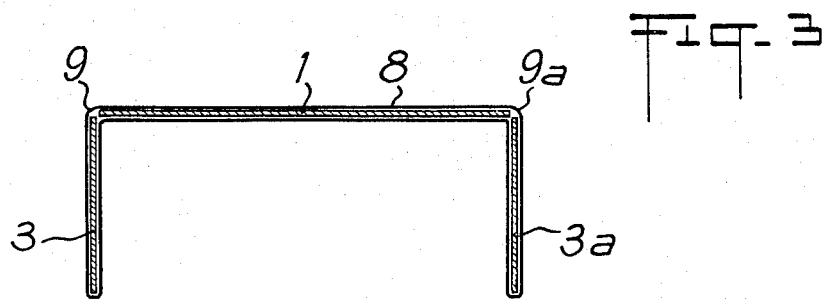
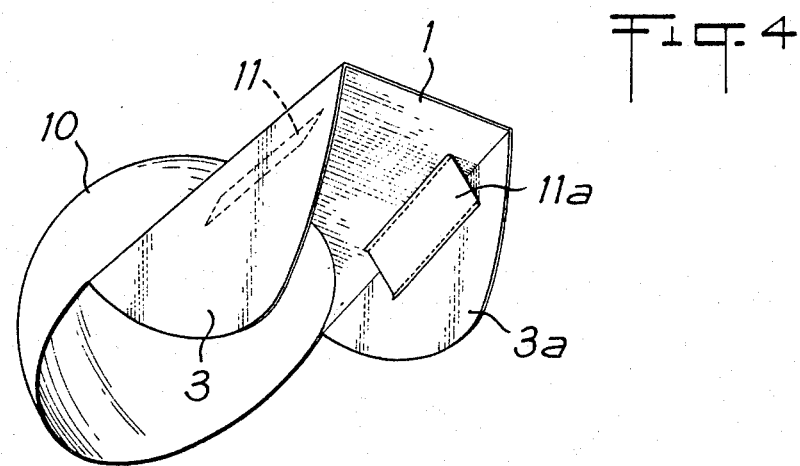
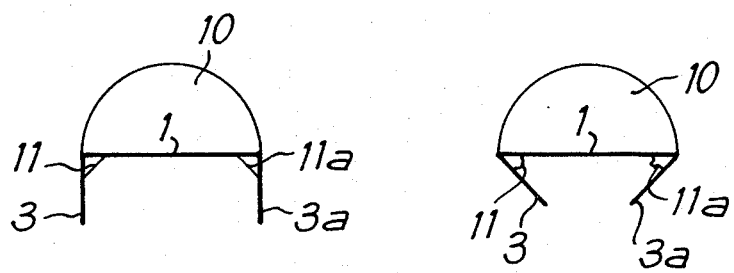
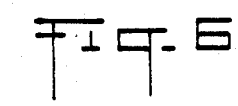

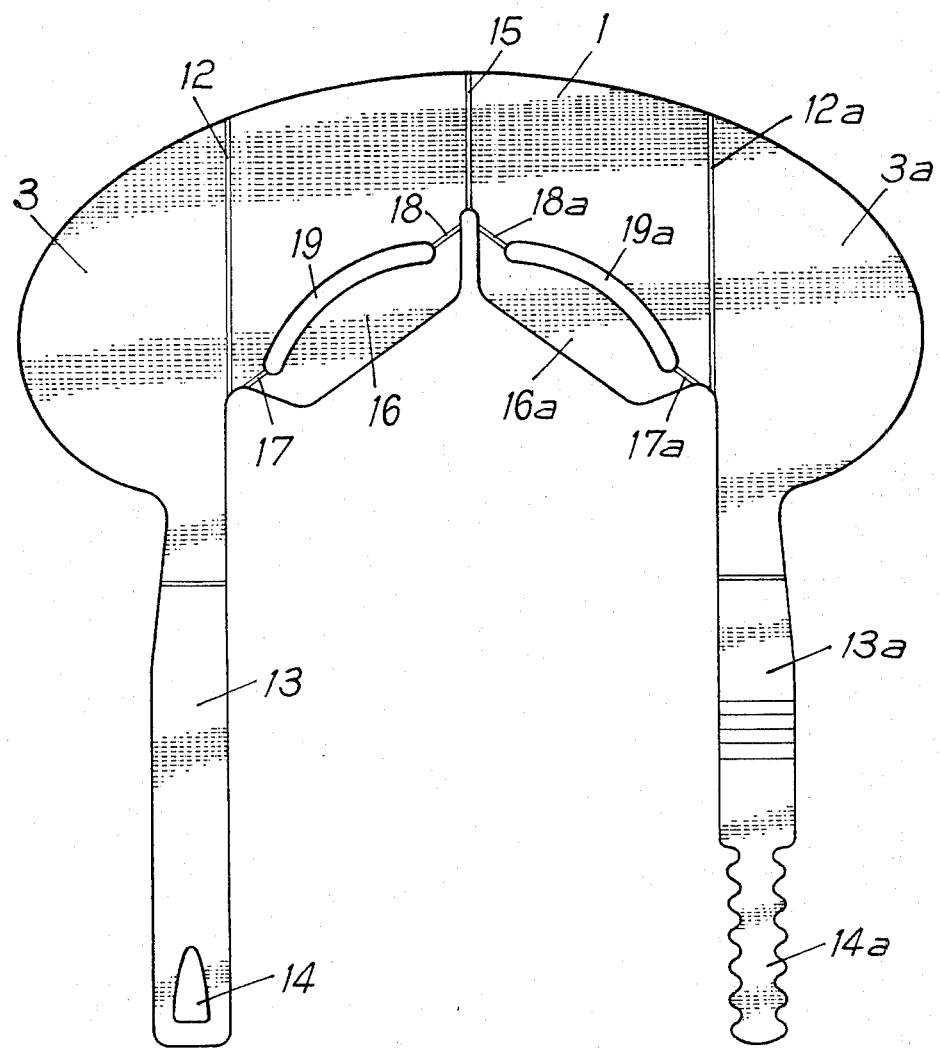

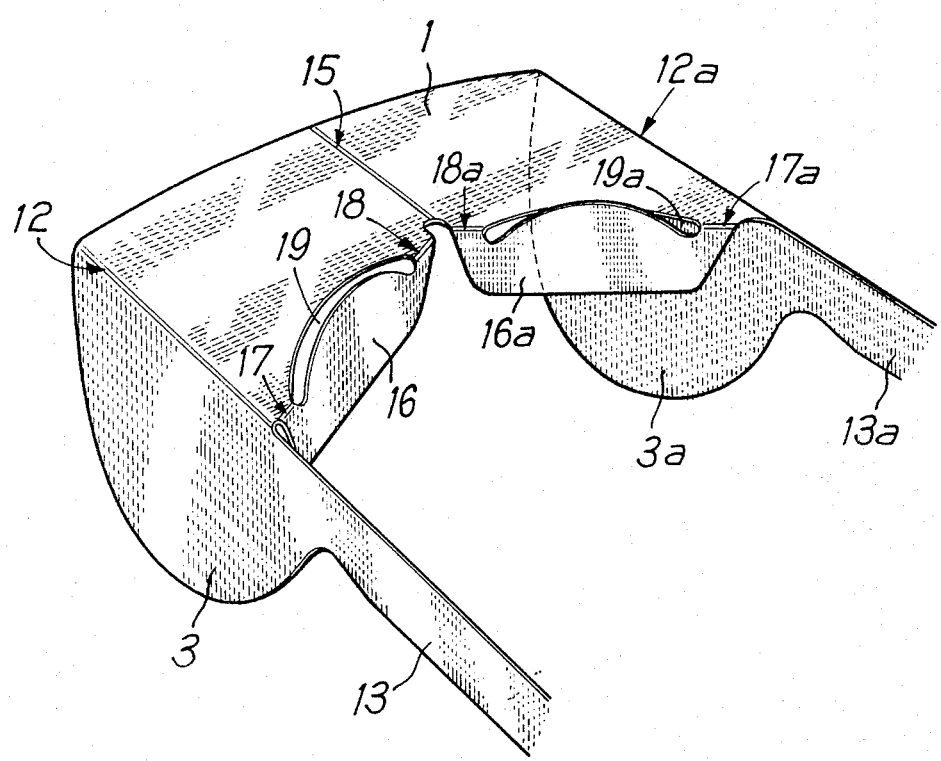

EYE-SHADES

BACKGROUND OF THE INVENTION

The present invention relates to eye-shades.

It is an object of the invention to provide an eye-shade particularly for use in practicing certain sports where the action is very fast, such as rifle and pistol shooting, and live and clay pigeon shooting where it is necessary to have the best possible view of a selected target and to be able to concentrate fully on this target in all circumstances.

SUMMARY OF THE INVENTION

To fulfill this and other objects, the invention provides an eye-shade comprising a substantially flat brow member, a temple member depending from each lateral portion of said brow member, and a head-encompassing member interconnecting said temple members to cause said brow member to extend outwardly in a substantially horizontal attitude above the wearer's eyes in the position of use with said temple members assuming a substantially vertical attitude, said brow member and said temple members defining a field of vision within the three faces constituted by said members, and means being provided to hold said temple members in position against the wearer's temples The eye-shade as a whole may be made all in one piece or may be made up in three parts four or five which are connected together by hinges in such a way that the eye-shade is easy to carry about, the lateral temple members folding under the brow member. An eye-shade according to the invention is very easy to produce since, if made all in one piece, it can be made in developed form; it can easily be cut out in the flat and then folded by the application of heat. Alternatively, if it consists of a number of parts, the various parts are cut out and either connected together by hinges or else arranged inside an envelope made of a flexible material.

The eye-shade may be fitted with a head band constituting the head encompassing member, which headband is connected to the temple members by a screw and nut system which allows the eye-shade to be adjusted in a vertical plane. Alternatively, the head-encompassing member may be in the form of a skull cap.

BRIEF DESCRIPTION OF THE DRAWINGS

Other features and advantages of the invention will be better understood from reading the following description of some embodiments thereof, with reference to the accompanying drawings, in which:

FIG. 1 is a perspective view of first embodiment of eye-shade in which the brow and temple members are in one piece, FIG. 2 is a perspective view of another embodiment of an eye-shade, which is fitted with hinges between the brow and temple members, FIG. 3 is a cross-sectional view of an eye-shade with the brow and temple members in three parts, and which is intended to be arranged in an envelope, FIG. 4 is a perspective view of another embodiment wherein the head-encompassing member is constituted by a skull cap, FIGS. 5 and 6 are views of an eye-shade which has elastic return means, FIG. 7 is a plan view of a cut-out blank used to produce an eye-shade, and FIG. 8 is a perspective view of an eye-shade obtained from the blank of FIG. 7.

DETAILED DESCRIPTION OF PREFERRED EMBODIMENTS

Referring now to the drawings, in FIG. 1 is shown an improved eye-shade according to the invention which consists of a brow member 1 which extends at its lateral edges 2, 2a into two lateral temple members 3, 3a which extend down below the brow member 1. The eye-shade so formed defines a field of vision bounded by members 1, 3, 3a, member 1 being substantially horizontal and members 3 and 3a being substantially vertical in the position of use.

A head-band 4 which is made of an elastic material and capable of being fitted around the user's head, is attached by its ends to the temple members 3 and 3a.

The band 4 is attached to the temple members by means of a system 5 of screws and nuts which allows the eye-shade to be adjusted in a vertical plane. The band 4 may also be fitted in a known way with means (not shown) for doing it up and adjusting it in length.

In the embodiment in FIG. 1 the eye-shade is made from a single sheet of plastics material such as the material known as "plastocel", which is folded under heat along edges 2, 2a. Also, the brow member 1 is provided along its rear edge with a bend 6 made of plastics foam which is intended to rest against the user's forehead.

The inside surfaces of the brow and temple members of the eye-shade are preferably matt and dark in colour.

In FIG. 2 is shown another embodiment of eye-shade in which the brow member 1 and the temple members 3, 3a are formed by three rigid plates. These plates are connected together by hinges 7, 7a which are made of a flexible material and the hinges may in particular be formed by strips of fabric which are bonded to brow member 1 and temple members 3, 3a, respectively.

When this is the case, it is possible for temple members 3, 3a to be folded horizontally underneath brow member 1 to make carrying easier.

In FIG. 3 is shown another embodiment in which all the members 1, 3 and 3a are formed by rigid plates which are arranged and secured in an envelope 8 made of a flexible material.

This envelope 8 may be made from sewn linen with the stitching between the brow member 1 and the lateral temple members 3, 3a marking the fold lines 9, 9a.

In FIG. 4 is shown an eye-shade in which the head-encompassing member is not a band, but a skull cap 10, the brow member and the two temple members being again shown at 1 and 3, 3a respectively. This embodiment is capable of being produced in the ways described above, i.e. either in one piece or in a number of pieces which are connected together by hinges.

Since in this embodiment there is no traction exerted by a band which can be employed to apply the vertical, lateral temple members 3, 3a against the user's temples, strips 11, 11a of a relatively flexible material (linen) are arranged inside the eye-shade, these being sewn or bonded to the brow member 1 and the temple members 3, 3a in the corners where the folds are situated.

As can be seen from FIGS. 5 and 6, these strips 11, 11a prevent the temple members 3, 3a from opening out by more than a right angle and ensure that they are held in position against the user's temples.

In FIG. 7 is shown a blank cut from a piece of reasonably pliable material such as a plastics material or cardboard. The blank has a first face 1 which extends into two faces 3, 3a which are intended to be folded back vertically, (FIG. 8) along two fold lines 12, 12a to form brow and temple members respectively and the said faces 3, 3a extend into arms 13, 13a constituting a head band, to attach the eye-shade to the user's head by end fastening means 14, 14a at the ends thereof.

In its central area the horizontal face 1 has a fold line 15 which enables the eye-shade to be folded in half for transport and handling.

In accordance with another feature, on one of the edges of the horizontal face 1 are provided two strips 16, 16a which connected to the said face along pairs of fold lines 17, 18 and 17a, 18a which are situated on either side of openings 19, 19a.

As shown in FIG. 8, strips 16, 16a are intended when folded along lines 17, 18 and 17a, 18a, to rest against the forehead of the user and for this reason they are capable of deforming in the centre so as to adapt to the curvature of the user's forehead.

Various modifications may of course be made by the man skilled in the art to the arrangements and methods which have just been described merely by way of non-limiting example without exceeding the scope of the invention. For example, the strips 16, 16a may be enlarged to form eye-pieces enabling the eye-shade to be used as rain or snow goggles or the like, eye-pieces protecting the wearer's eyes against the weather and the brow member 1 minimising the in-fall of rain snow on to the eye-pieces.

I claim:

1. An eye-shade comprising a one piece blank defining a substantially flat brow member having a fold line in a central portion thereof allowing the brow member to be folded in half, a pair of temple members respectively connected to the brow member along a pair of laterally spaced fold lines at opposite sides of the brow member, and a pair of intergral arms respectively extending from said temple members along another pair of fold lines to free ends, said free ends defining cooperating means for securing said arms together thereby to provide a head-encompassing member interconnecting said temple members to cause said brow member to extend outwardly in a substantially horizontal attitude above the wearer's eyes in the position of use with said temple members assuming a substantially vertical attitude; said brow member including an inner edge between said arms and a pair of integral forehead strips forming part of said one piece blank and being foldably connected to said brow member on each side of the fold line in the brow member along a pair of angularly related fold lines, said blank having an opening formed therein along each of said angularly related fold lines to allow said forehead strips to be folded downwardly with respect to said brow member and deform to adapt to the curvature of the wearer's forehead; said brow member and said temple members defining a field of vision within the three sidewalls defined by said members.

2. An eye-shade according to claim 1, which is provided on the inside with two return members which are attached to said temple members and said brow member respectively to restrict the extent to which the temple members can open.

* * * * *